Figures 1, 2:
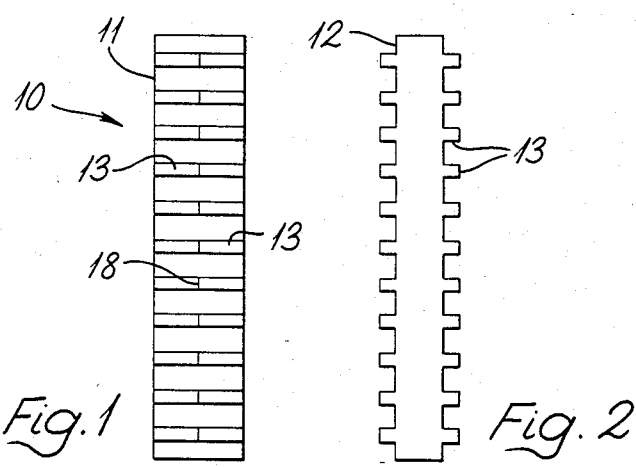

United States Patent [19]

Evans et al.

[11] Patent Number: 4,516,569

[45] Date of Patent: May 14, 1985

[54] INTRAMEDULLARY ORTHOPAEDIC DEVICES

[75] Inventors: David M. Evans, Farnham Common; Barry O. Weightman, Thames Ditton, both of England

[73] Assignee: National Research Development Corporation, London, England

[21] Appl. No.: 492,034

[22] Filed: May 5, 1983

[30] Foreign Application Priority Data

May 6, 1982 [GB] United Kingdom ............... 8213032

[51] Int. Cl.³ .............................................. A61F 5/04
[52] U.S. Cl. .............................. 128/92 BC; 128/92 B
[58] Field of Search ........... 128/92 BC, 92 D, 92 CA, 128/92 B; 3/1.91, 1.9

[56] References Cited

U.S. PATENT DOCUMENTS

| | | | |
|---|---|---|---|
| 2,136,471 | 11/1938 | Schneider | 128/92 BC |
| 2,518,019 | 8/1950 | Kane | 128/92 BC |
| 2,675,801 | 4/1954 | Bambara et al. | 128/92 BC |
| 2,719,522 | 10/1955 | Hudack | 128/92 CA |
| 2,821,979 | 2/1958 | Cameron | 128/92 BC |
| 3,681,786 | 8/1972 | Lynch | 3/1.91 |
| 4,103,683 | 8/1978 | Neufeld | 128/92 BC |
| 4,135,506 | 1/1979 | Ulrich | 128/92 D |
| 4,204,284 | 5/1980 | Koeneman | 3/1.91 |
| 4,262,665 | 4/1981 | Roalstad et al. | 128/92 BC |
| 4,275,717 | 6/1981 | Bolesley | 128/92 BC |
| 4,304,011 | 12/1981 | Whelan | 3/1.91 |
| 4,364,382 | 12/1982 | Mennen | 128/92 D |

FOREIGN PATENT DOCUMENTS

| | | |
|---|---|---|
| 0041591 | 12/1981 | European Pat. Off. . |
| 1582450 | 1/1981 | United Kingdom . |
| 1603868 | 12/1981 | United Kingdom . |

*Primary Examiner*—C. Fred Rosenbaum
*Assistant Examiner*—C. W. Shedd
*Attorney, Agent, or Firm*—Cushman, Darby & Cushman

[57] ABSTRACT

An intramedullary orthopaedic device for interconnecting bone fragments for union comprises an elongate member of plastics material having a relieved structure extending over its length but only partially therearound, each upstanding element being of transverse sizing to afford an interference fit by translation alone into a slightly undersized bone recess, such fit resulting from flexure of the elements without stripping bone material, and the unrelieved area of the member being of non-circular cross-section to inhibit rotation. The member is suitably of rectangular cross-section with sequences of fins having their longitudinal directions across the major side faces, and with the inter-sequence spacing and fin height each exceeding fin thickness.

6 Claims, 5 Drawing Figures

INTRAMEDULLARY ORTHOPAEDIC DEVICES

This invention concerns endoprosthetic devices and relates more particularly to such devices for the interconnection of bone fragments to stabilise the same during bone union between those fragments.

Various forms of device are available for this purpose, including intramedullary pins and nails, bone plates, and external fracture fixation frames. However, while these available devices are in widespread routine usage, particularly in connection with the longer bones of the limbs, there is room for an improved device for use with smaller bones such as those of the finger.

According there is provided an endoprosthetic orthopaedic device comprising an elongate member of plastics material having a relieved structure extending axially thereover, but only partially transversely therearound, each upstanding element of said structure being of cross-sectional dimensions as to allow securement of said member in an interference fit in bone by translation alone into a pre-prepared substantially complementary recess in the bone, such fit resulting from flexure of said structure without stripping of bone material from the wall of said recess, and the unrelieved axial surface area of said member being of non-circular cross-sectional shape to inhibit rotation thereof in said recess.

The proposed device has been developed from one described in U.S. Pat. No. 4,231,120. This earlier device is generally similar to that at hand, but has so far only been employed in a circular cylindrical form with a relieved structure extending over substantially the whole of its length and wholly around its circumference. Consideration was in fact given to use of the device of this last form for the present purpose but, notwithstanding its securement capabilities in bone, a rotational movement can occur. It is likely in practice that this movement will be limited to that possible within the remanent flexure of the relieved structure, and so be small. Also, such movement has been rendered effectively negligible by the use to date of a pair of members in a device of the earlier form for the securement of an articular bone joint component. However, use of the presently proposed device will normally involve a single member and even a small rotation movement is undesirable.

In the present device, each non-circular portion of the cross-sectional shape of the member is preferably rectilinear. More specifically the overall cross-sectional shape of the member is preferably rectangular and defined by an opposed pair of relieved faces and another such pair of unrelieved faces, with the relieved faces forming the major sides of the rectangular shape.

Also, as with the earlier device, the relieved structure is suitably of finned form consisting of sequences of fins of which the longitudinal directions extend transversely of the member, with each sequence including a plurality of separate fins. The cross-sectional dimensions and spacing of these fins are to be determined as before in dependence upon the mechanical properties of the plastics material used and those of bone. In general the fin sequences will be successively spaced axially of the member by a distance which is greater than the individual fin thickness in that axial direction, and the fin height will be greater than such thickness. Again, ultra high molecular weight polyethylene is presently preferred, although others such as polypropylene are suitable.

Normally a member as now proposed will be smaller in overall cross-sectional form than previously, with a correspondingly reduced finned structure. Following initial development, devices undergoing tests comprise a member having an elongate core of rectangular cross-section with dimensions up to about 5 mm by 2 mm, and fins of up to about 0.3 mm thickness, 4 mm length, 1.0 mm height, and 1.0 mm inter-fin spacing axially of the member, the sequence being located on the major side faces of the member.

Figure 3:
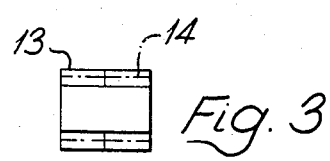
Figure 4:
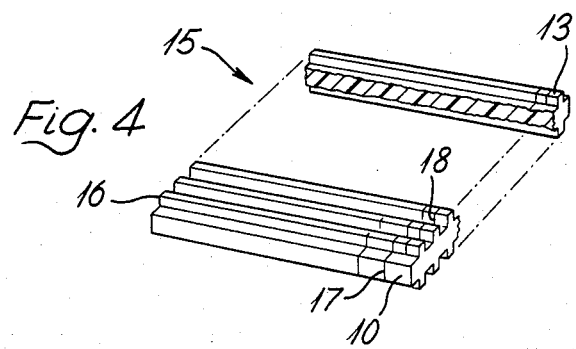

The form of the invention as so far developed is clarified by the accompanying drawings, in which:

FIGS. 1, 2 and 3 are mutually perpendicular side elevations and an end elevation, respectively, of one embodiment of a member as just described, FIG. 4 illustrates a manufacturing procedure for members such as that of FIGS. 1 to 3, and FIG. 5 schematically illustrates another form of member according to the present invention.

The embodiment of FIGS. 1 to 3 is intended primarily for the securement of fractures in finger bones and is constituted by an elongate member 10 made in one piece from ultra high molecular weight polyethylene. The member 10 has an overall cross-sectional shape which is rectangular, and a solid core portion 11 of similar shape. Each of the major side faces 12 has thereover a like relieved structure consisting of sequences of fins 13, with each sequence consisting of two like fins extending in end-to-end manner transversely across the whole width of the relevant face, and with the sequence being uniformly spaced axially along the face.

While it is clear that this embodiment can be made in a range of sizes, it is useful to give the dimensions for one size to indicate the proportions. Thus, in one size, the core cross-section is 4 mm by 2 mm, the fins are each 0.3 mm thick, 1.0 mm high, and 2 mm long, and the inter-fin spacing is 1.0 mm. The length of the member can also be in a range of sizes, but may conveniently be made to a maximum usable size and cut to any desired lesser length at the time of use.

In an alternative form of this embodiment there are not two fins each of 2 mm length in each sequence, but a single fin of 4 mm length. Also a larger size of the same two-fin sequence form, with 5×2 mm dimensions and 2.5 mm fins is undergoing trial.

In use of such a member, the bone fragments of a fractured bone will be prepared with respective individual recesses extending longitudinally thereinto from the fracture site. These recesses will each be substantially the same cross-sectional form as the member, but slightly less across the narrower dimension transversely across the fins as indicated in chain line at 14 in FIG. 3. Also the recesses will be aligned when the bone fragments are brought together in the desired position for union. Following this preparation, one end of the member is pushed into one recess, cut to the required length, and the fragments then brought together to engage the other end of the member in the other recess, with the fragments in abutment.

FIG. 4 illustrates a convenient manufacturing procedure for members as just described in which an appropriate slab 15 of plastics material is machined to produce fins 16 across its major faces, and the slab and fins are thereafter cut at 17 and 18 to separate individual members 10 and fins 13.

It will be appreciated that while the illustrated embodiment represents a presently preferred form of the invention as so far developed, other forms are possible.

For example, the relieved structure is not essentially of a finned form and alternatives to a rectangular cross-section are possible.

Figure 5:
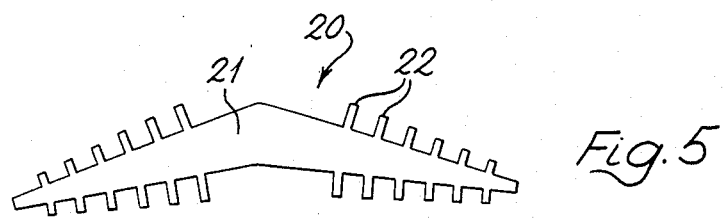

Also, while reference has been made to initial development for fracture fixation, particularly in the finger, the invention can find application in various situations requiring securement of small bone fragments. One example of another situation involves arthrodesis of finger joints and FIG. 5 schematically represents a modified form of member 20 for this purpose. This modified member is generally similar to that described above in having an elongate core 21 and transverse fins 22 on two opposed faces, but in this case the member is tapered towards its longitudinal ends from the centre where it is angled, and the fins are also correspondingly reduced in height along the member. The angled form of the member gives rise to similar angling at the arthrodesed joints as is common practice for fingers.

Lastly, reference has been made to manufacture by machining but other, moulding techniques are possible and may well be preferred. More specifically, compression moulding of ultra high molecular weight polyethylene and polypropylene is possible and is suited to members such as that of FIG. 5.

We claim:

1. An internal orthopaedic fracture fixation device for a small bone comprising:

an elongate member of plastics material, said member having a rectangular overall cross-sectional shape defined by an opposed pair on major side faces in alternating disposition with an opposed pair of minor side faces;

said minor side faces being smooth;

said major side faces being formed over at least a major portion of the length thereof with at least two longitudinally adjacent sequences of fins;

each said sequence:

having the longitudinal direction of the fins therein extending transversely of said member, being spaced longitudinally on said member from the next adjacent one of said sequences by a distance greater than the thickness of a respective one of said fins in the same direction, and having the height of each said fin, directed outwardly from said member, being greater than said thickness;

said member being constructed and arranged to be secured by an interference fit, by longitudinal translation alone, into a preprepared, substantially complementary recess in said small bone; with such fit resulting from flexure of said fins of at least one corresponding said sequence thereof on each said major side face without necessarily causing substantial stripping of bone material from the wall of said recess, while said smooth faces act against rotation of said member in said recess.

2. A device according to claim 1 wherein said member comprises an elongate core of rectangular cross-section with dimensions up to about 5 mm by 2 mm, and fins of up to about 0.3 mm thickness, 4 mm length, 1.0 mm height and 1.0 mm inter-fin intra-sequence spacing axially longitudinally of said member.

3. A device according to claim 2 wherein said core dimensions are uniformly 4 mm by 2 mm, said fins are each 0.3 mm thick, 1.0 mm high and 2 mm long, said inter-fin spacing is 1.0 mm and there are a pair of such fins in end-to-end relation across each major face of said member in each said fin sequence.

4. A device according to claim 2 wherein said core dimensions are uniformly 4 mm by 2 mm, said fins are each 0.3 mm thick, 1.0 mm high and 2 mm long, said inter-fin spacing is 1.0 mm, and there is a single fin across each major face of said member in each said fin sequence.

5. A device according to claim 2 wherein said core dimensions are uniformly 5 mm by 2 mm, said fins are each 0.3 mm thick, 1.0 mm high and 2.5 mm long, said inter-fin spacing is 1.0 mm, and there are a pair of such fins in end-to-end relation across each major face of said number in each said fin sequence.

6. A device according to claim 1 wherein said member is longitudinally tapered towards each end from an intermediate portion thereof.

* * * * *